United States Patent [19]

Smith, Jr. et al.

[11] Patent Number: 4,918,243

[45] Date of Patent: Apr. 17, 1990

[54] HEAT INTEGRATION PROCESS

[75] Inventors: Lawrence A. Smith, Jr., Bellaire; Edward M. Jones, Jr., Friendswood; Dennis Hearn, Houston, all of Tex.

[73] Assignee: Chemical Research & Licensing Company, Houston, Tex.

[21] Appl. No.: 263,812

[22] Filed: Oct. 28, 1988

[51] Int. Cl.$^4$ .............................................. C07C 41/06
[52] U.S. Cl. ...................................... 568/697; 203/21
[58] Field of Search ........................... 568/697; 203/21

[56] References Cited

U.S. PATENT DOCUMENTS 4,198,530  4/1980  Wentzheimer ....................... 568/697
4,324,924  4/1982  Torck et al. ............................ 568/697

Primary Examiner—Howard T. Mars
Attorney, Agent, or Firm—Kenneth H. Johnson

[57] ABSTRACT

A portion of the best of vaporization, required to separate and recover methanol from wash water used to remove methanol from a $C_4$ raffinate resulting from the reaction of isobutene containing $C_4$ hydrocarbons and methanol to produce MTBE is recovered by conducting the distillation of the methanol/water mixture at a pressure of 40 to 60 psig, thereby increasing the temerature of the methanol overhead to 104° to 114° C. and using the reaction effluent from the MTBE reactor to cool and condense the methanol overhead, said reactor effluent being correspondingly heated prior to entry into a debutanizer tower where unreacted $C_4$'s and methanol are removed as a raffinate and MTBE product recovered. It is this raffinate that is washed with water to recover the unreacted methanol, with the methanol/water mixture being distilled as set forth above. In another embodiment a stream having a lower temperature than the methanol overhead is withdrawn from the debutanizer and used to cool the methanol overhead, then the correspondingly heated stream returned to the debutanizer.

8 Claims, 2 Drawing Sheets

HEAT INTEGRATION PROCESS

BACKGROUND OF THE INVENTION

1. Field of the Invention

The present invention relates to a method for recovering the heat of vaporization of the methanol recovery section of a methyl tertiary butyl ether (MTBE) plant.

2. Related Art

The production of methyl tertiary butyl ether (MTBE) is usually carried out by selectively reacting isobutene contained in a refinery $C_4$ stream with methanol in the presence of an acid catalyst. The resulting MTBE product is separated from the $C_4$ stream which is then potentially useful for other purposes such as alkylation.

The separation of MTBE from the hydrocarbon product stream is not a problem because of the boiling point difference between MTBE and $C_4$, the DME and methanol are lower boiling and contaminate the $C_4$ fraction.

The recovery and recycle of unreacted methanol is essential to the economics of the overall conventional MTBE process. Notwithstanding the particular MTBE reaction system used for the direct reaction of methanol with isobutene in mixed $C_4$ streams, it may be necessary to employ a water wash to separate methanol from the unreacted $C_4$, since the $C_4$'s form azeotropes with methanol and a clean separation cannot be obtained by distillation alone.

The removal of methanol from the $C_4$'s can be carried out with a water wash system, since methanol is relatively soluble in water, and the methanol can be readily separated by distillation from the water, which is a conventional procedure. The problem is the loss of energy required to distill the methanol. The distillation of methanol from the wash water is presently conducted at low pressure. Under the usual pressure conditions the methanol overhead condenses at around 65° to 71° C.

SUMMARY OF THE INVENTION

The present invention is an improvement in the preparation of methyl tertiary butyl ether comprising feeding an isobutene containing $C_4$ feed stream into a reactor, contacting said feed stream and methanol in the presence of an acidic catalyst to preferentially react at least a portion of the isobutene and methanol to form methyl tertiary butyl ether, separating said methyl tertiary butyl ether from unreacted $C_4$'s and methanol by distillation (debutanizer tower), recovering a stream containing unreacted $C_4$'s and methanol, contacting said unreacted $C_4$ stream with water to remove methanol therefrom (preferably the weight ratio of water : hydrocarbon is from about 0.1:1 to 0.4:1), recovering a methanol water mixture and distilling said methanol/water mixture to remove methanol therefrom as an overhead; wherein the improvement comprises conducting the distillation of said methanol/water mixture at a pressure in the range of 40 to 60 psig, whereby the temperature of the methanol overhead is from about 104° to 114° C., said methanol overhead being condensed by indirect heat exchange between said methanol overhead and said debutanizer feed stream, said feed stream having a lower temperature than said methanol overhead, thereby preheating the debutanizer feed stream and cooling and condensing the methanol overhead. In another embodiment, the methanol overhead may be condensed by indirect heat exchange with the mixture undergoing distillation in the debutanizer tower by using a said reboiler at a point where the column temperature is low enough to exchange heat with the methanol overhead.

The ordinary distillation of methanol from the wash water, at lower pressure (atmospheric up to a few pounds of pressure), produces a methanol overhead of about 65° C. which because of the equilibrium in heat exchangers is not very useful for heating. The present invention provides a more useful heat source, and for recovery of a portion of the heat of vaporization required for the methanol separation. Where high pressure steam is available without a premium as compared to low pressure steam then the present invention present a clear advantage. In any event the ability to recover a portion of the heat of methanol vaporization in the process (i.e., by preheating the debutanizer tower feed) may make the present process advantageous not withstanding the need for a higher temperature heat source in the methanol/water distillation column.

In the present invention the debutanizer tower feed stream is at a lower temperature than the methanol overhead. The temperature of the debutanizer tower feed stream or the draw stream from the tower can vary widely but the differential between the temperature of the stream in question and the methanol overhead will be at least 10° C. and preferably from 10° to 30° C.

DETAILED DESCRIPTION OF THE INVENTION AND PREFERRED EMBODIMENTS

Figure 1:
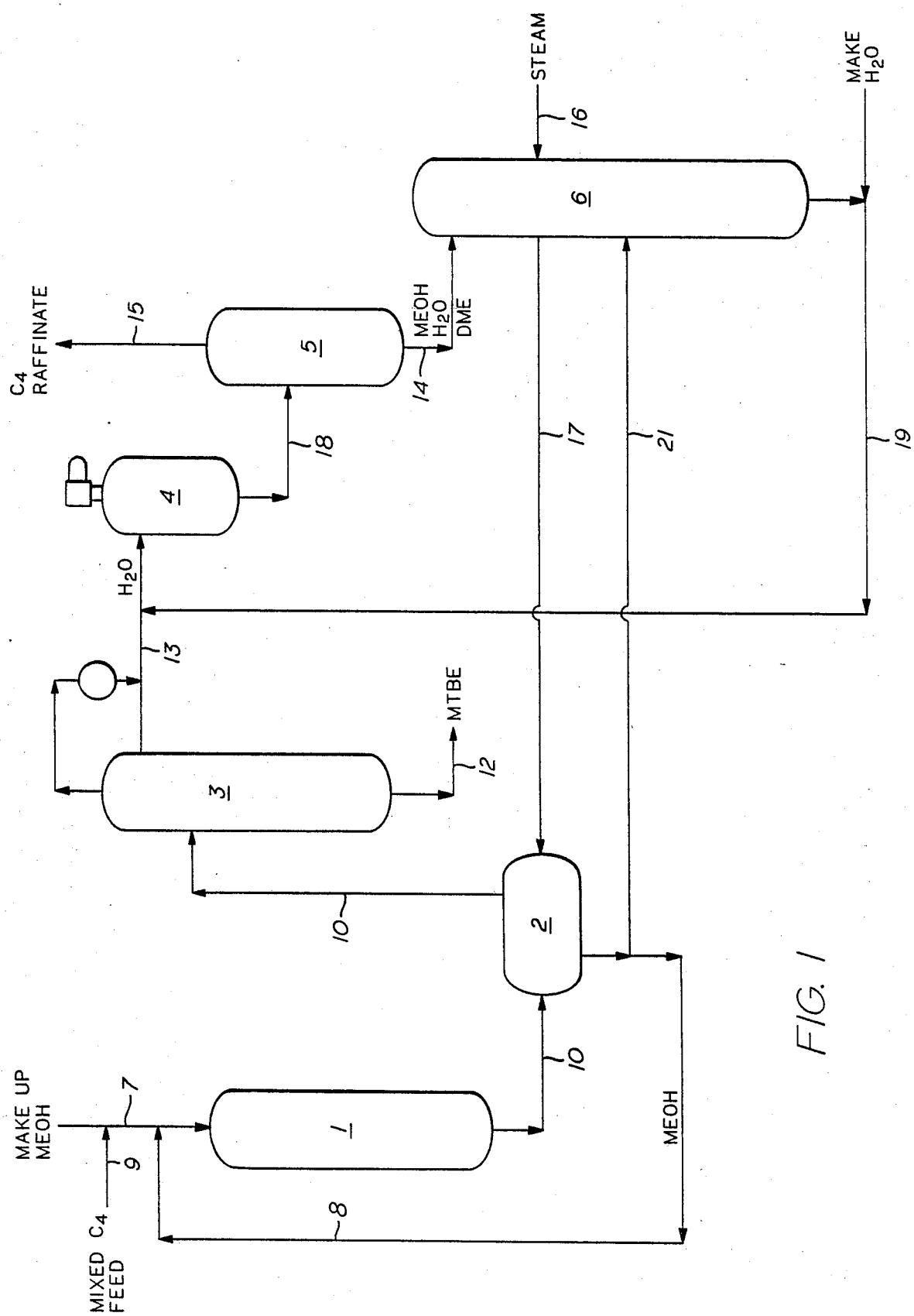
FIG. 1 is a schematic representation of an MTBE manufacturing system employing one embodiment of the present invention.

The present invention may be used with any of the reactors or methods of producing MTBE known in the art, comprising reacting methanol with isobutene in a mixed $C_4$ stream where it is desirable or necessary to increase the temperature of the reactor stream for separation of MTBE from $C_4$ and methanol by distillation. The methanol may be present in stoichiometric amounts or in excess or deficiency thereof based on the isobutene in the $C_4$ feed. The reaction of isobutene and methanol is selective, that is, the n-butenes are far less reactive than the isobutene. The acid catalyst now widely used are the acidic cation exchange resins.

The reaction to produce the ether and thereby separate and remove the isobutene from the $C_4$ stream may be carried out in any of the reactors used in the art. That is the reaction may be carried out in fixed bed reactors under pressure to maintain the liquid phase, for example, as described in U.S. Pat. No. 4,071,567, Ancillotti, et al. or in a catalytic distillation column as described in the U.S. Pat. No. 4,336,407 Smith.

The product from either a single reactor or a series of reactors may be separated by conventional distillation, by recovering the ether as a bottom product and unreacted feed components as overheads.

The catalyst, preferably an acidic cation exchange resin, is loaded into a reactor as a fixed bed of the granules. The feed to the reaction is fed to the bed in liquid phase. The bed may be horizontal, vertical or angled.

Preferably bed is vertical with the feed passing downward through the bed and exiting, after reaction, through the lower end of the reactor.

Preferred and conventional catalysts for the etherification are acidic cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenylether and others. The polymers may be prepared in the presence or absence of solvents or dispersing agents, and various polymerization initiators may be used, e.g., inorganic or organic peroxides, persulfates, etc.

The resulting product preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Publication No. 908,247).

The ion exchange resin is preferably used in a granular size of about 0.25 to 1 mm, although particles from 0.15 mm up to about 1 mm may be employed. The finer catalysts provide high surface area, but also result in high pressure drops through the reactor. The macroreticular form of these catalysts is preferred because of the much larger surface area exposed and the limited swelling which all of these resins undergo in a non-aqueous hydrocarbon medium.

Similarly, other acid resins are suitable, such as perfluorosulfonic acid resins greater detail in DuPont "Innovation", Volume 4, No. 3, Spring 1973 or the modified forms thereof as described in U.S. Patent Nos. 3,784,399; 3,770,567 and 3,849,243.

In the selective etherification of isobutene with methanol, usually a stoichiometric amount or an excess (based on isobutene) is employed in order to obtain the highest conversion of isobutene possible. In these cases, unreacted methanol is a substantial problem in the unreacted $C_4$ raffinate. However, even when about 10% less than the stoichiometric amount of methanol is employed some methanol may not be reacted and a contamination of the $C_4$ raffinate with methanol may occur, but is substantially less significant. Hence the present invention is primarily concerned with etherification wherein from about 10% less to an excess of the stoichiometric amount of methanol based on isobutene in the $C_4$ hydrocarbon is employed. Methanol in 100% or more, e.g. 200%, stoichiometric excess may be employed. Preferably the amount of methanol in etherification process is from slightly less than stoichiometric to about 50% excess based on the isobutene present.

The $C_4$ hydrocarbon streams employed as the feed to the etherifications, normally contain 5 to 60 wt % isobutene with the remainder being normal butane, normal butenes, isobutane and some small amounts of $C_3$ and $C_5$ hydrocarbons. The isobutene will preferentially and selectively react with methanol in the presence of acidic catalyst to form MTBE. The temperature of the $C_4$ hydrocarbon feed stream is generally in the range of 35° to 80° C.

Referring now to FIG. 1, the MTBE plant may be any of those described, but for this illustration a fixed bed reactor will be described. A mixed $C_4$ feed 9 containing 11 wt % isobutene with remainder primarily n-butene, n-butane and isobutane is fed to reactor 1 with make methanol and recycle methanol 8. The methanol is fed at a stoichiometric excess (38% excess). The conversion of isobutene is 93% thus leaving only about 0.85% isobutene in the total unreacted $C_4$'s. The MTBE is separated from the reaction mixture, i.e., the effluent 10, by distillation in debutanizer tower 3 and recovered as a bottom 12. The $C_4$ raffinate 13 containing about 3 wt % methanol is recovered from debutanizer 3 and contacted with water (Water:HC weight ratio about 0.21:1) in a mixer 4 hence the mixed hydrocarbon/water stream 18 goes to separator 5 where the $C_4$ raffinate 15 is recovered substantially free of methanol by decanting and the water containing methanol (about 15 wt % methanol) dimethyl ether and some hydrocarbons 14 goes to distillation column 6 which is operated at 50 psig overhead pressure. Steam 16 (16° C., 75 psig) is injected in to column 6 and the temperature of the overhead 17 which is 99.9+ methanol is 110° C. The overhead 17 is condensed in condenser/heat exchanger 2 by indirect contact with reactor effluent 10 (which is at an inlet temperature of about 70° C. and exit temperature of about 80° C.). The condensed methanol 8 is now at about 80° C. and is recycled to reactor 1 where make up methanol 7 is added.

A portion of the condensed methanol is returned via line 21 to column 6. The water separated and recovered in column 6, may be recycled via 19 to mixer 4. Make-up water may also be added through 19.

The heated reactor effluent 10 is fed to the debutanizer tower 3. The debutanizer is operated in any suitable manner to obtain a separation by distillation of the MTBE from the other components of the reactor effluent 10 Thus by employing a high pressure distillation of methanol water wash, it is possible to recover some of the heat of the distillation, whereas using a conventional distillation at 5 psig for example the temperature of the methanol overhead 17 would have been only 74° C. which is only 4° C. greater than the incoming reactor effluent 10—not a sufficient differential to raise the temperature of the effluent.

Figure 2:
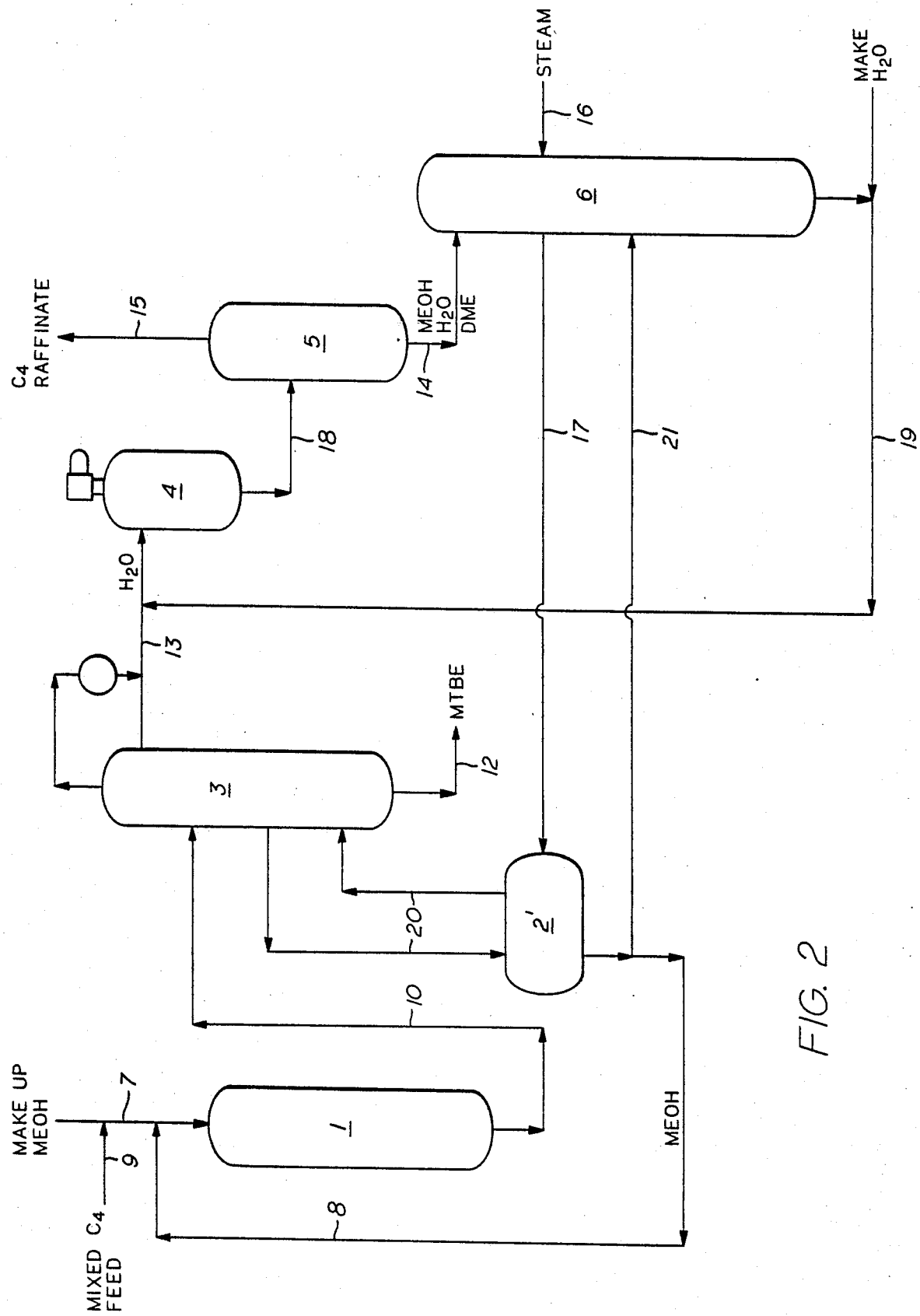
FIG. 2 is a schematic representation an alternative embodiment of the present invention.

In FIG. 2 the alternative embodiment is depicted with 2′ being a reboiler. A portion of the material from debutanizer tower 3 is withdrawn recirculated through reboiler 2′ via line 20 where it is indirectly contacted with the methanol overhead from column 6. The material withdrawn is at a lower temperature than the methanol overhead, in the manner as described for the embodiment of FIG. 1. For example a stream withdraw for the debutanizer 3 may be at 75° and the methanol overhead at 114° and a temperature exchange of a similar degree as in the embodiment of FIG. 1 obtained.

The invention claimed is:

1. In the process for the preparation of methyl tertiary butyl ether comprising feeding an isobutene containing $C_4$ feed stream into a reactor, contacting said feed stream and methanol in the presence of an acidic catalyst to preferentially react at least a portion of the isobutene and methanol to form methyl tertiary butyl ether recovering a reactor effluent comprising said methyl tertiary butyl ether, feeding said reactor effluent to a distillation tower, separating said methyl tertiary butyl ether from unreacted $C_4$ hydrocarbons and methanol by distillation in said tower, recovering a raffinate containing unreacted $C_4$ hydrocarbons and methanol, contacting said raffinate with water to extract methanol into said water, separating said raffinate and water, recovering a methanol/water mixture and distilling said methanol/water mixture to remove methanol therefrom as an overhead; wherein the improvement comprises conducting the distillation of said methanol/water mixture at a pressure in the range of 40 to 60 psig, whereby the temperature of the methanol overhead is from about 104° to 114° C., said methanol overhead being condensed by indirect heat exchange between said methanol overhead and a stream withdrawn from said distillation tower, said withdrawn stream having a lower temperature than said methanol overhead prior to said indirect contact, thereby heating said withdrawn stream and cooling and condensing the methanol overhead, and returning said withdrawn stream to said distillation tower after said indirect heat exchange.

2. The process according to claim 1 wherein the temperature differential between said withdrawn stream and said methanol overhead is at least 10° C.

3. The process according to claim 2 wherein the temperature of said withdrawn stream is in the range of 35° to 80° C.

4. The process according to claim 3 wherein the methanol is present in the reaction to form methyl tertiary butyl ether in an amount of from about 10% less to 100% or more above the stoichiometric amount based on isobutene present in said $C_4$ hydrocarbon feed.

5. The process according to claim 3 wherein the methanol is present in the reaction to form methyl tertiary butyl ether in an amount of from slightly less to about 50% about the stoichiometric amount based on isobutene present in said $C_4$ hydrocarbon feed.

6. The process according to claim 1 wherein water from the distillation of said methanol/water mixture is recycled to contact said raffinate.

7. The process according to claim 4 wherein the methanol is present in the reaction to form methyl tertiary butyl ether in an amount of from slightly less to about 50% above the stoichiometric amount based on isobutene present in said $C_4$ hydrocarbon feed.

8. The process according to claim 7 wherein water from the distillation of said methanol/water mixture is recycled to contact said raffinate.

* * * * *